US010463763B2

(12) United States Patent
McKay

(10) Patent No.: US 10,463,763 B2
(45) Date of Patent: Nov. 5, 2019

(54) DEMINERALIZED BONE MATRIX WITH IMPROVED OSTEOINDUCTIVITY

(71) Applicant: Warsaw Orthopedic, Inc., Warsaw, IN (US)

(72) Inventor: William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 15/906,788

(22) Filed: Feb. 27, 2018

(65) Prior Publication Data

US 2018/0185548 A1 Jul. 5, 2018

Related U.S. Application Data

(62) Division of application No. 14/256,069, filed on Apr. 18, 2014, now Pat. No. 9,907,882.

(51) Int. Cl.
| | | |
|---|---|---|
| *A61K 35/14* | (2015.01) | |
| *A61L 27/36* | (2006.01) | |
| *A61L 27/54* | (2006.01) | |

(52) U.S. Cl.
CPC ......... *A61L 27/3683* (2013.01); *A61L 27/365* (2013.01); *A61L 27/3608* (2013.01); *A61L 27/54* (2013.01); *A61L 2430/02* (2013.01)

(58) Field of Classification Search
None
See application file for complete search history.

(56) References Cited

U.S. PATENT DOCUMENTS

| | | | |
|---|---|---|---|
| 5,236,456 A * | 8/1993 | O'Leary | A61F 2/30767 128/DIG. 8 |
| 5,580,923 A | 12/1996 | Yeung et al. | |
| 5,700,289 A * | 12/1997 | Breitbart | A61L 27/3804 424/423 |
| 5,795,584 A | 8/1998 | Totakura et al. | |
| 6,189,537 B1 * | 2/2001 | Wolfinbarger, Jr. | A61F 2/28 128/898 |
| 6,294,157 B1 | 9/2001 | Rubinstenn et al. | |
| 6,305,379 B1 * | 10/2001 | Wolfinbarger, Jr. | A61F 2/28 128/898 |
| 6,899,107 B2 | 5/2005 | Lewandrowski et al. | |
| 8,202,539 B2 | 6/2012 | Behnam et al. | |
| 2007/0260299 A1 | 11/2007 | Gagnieu | |
| 2007/0280990 A1 | 12/2007 | Stopek | |
| 2008/0254091 A1 | 10/2008 | Lee et al. | |
| 2009/0226523 A1 * | 9/2009 | Behnam | A61L 27/3608 424/488 |
| 2010/0203155 A1 * | 8/2010 | Wei | A61F 2/4603 424/549 |
| 2012/0040928 A1 | 2/2012 | Bansal | |

OTHER PUBLICATIONS

Mathias P. G. Bostrom, MD & Daniel A. Seigerman, The Clinical Use of Allografts, Demineralized Bone Matrices. Synthetic Bone Graft Substitutes and Osteoinductive Growth Factors: A Survey Study, Hospital for Special Surgery 2005, HSSJ (2005) 1:9Y18. DOI 10.1007/s11420-005-0111-5, 10 pages.
George F. Muschler, MD, Hironori Nitto, MD, PHD§, Yoichi Matsukura, MD, PHD§, Cynthia Boehm, BS, Antonio Valdevit, MS, Helen Kambic, MS, William Davros, PHD⁑, Kimberly Powell, PHD, and Kirk Easley, MS‡, Spine Fusion Using Cell Matrix Composites Enriched in Bone Marrow-Derived Cells, NIH Public Access, Author Manuscript, Clin Orthop Relat Res. Author manuscript; available in PMC Apr. 4, 2006, 22 pages.
George F. Muschler, MD,⁑, A, Yoichi Matsukura, MD, PHD⁑, Hironori Nitto, MD, PHD⁑, Cynthia A. Boehm, BS†, Antonio D. Valdevit, MS;†, Helen E. Kambic, PHD;⁑, William J. Davros, PHD ‡ , Kirk A. Easley, MS§, and Kimerly A. Powell, PHD;⁑, Selective Retention of Bone Marrow-Devrived Cells to Enhance Spinal Fusion, NIH Public Access, Author Manuscript Clin Orthop Relat Res. Author manuscript; available in PMC Apr. 4, 2006, 18 pages.
Emily J. Arnsdorf, M.S., Luis M. Jones, M.S., Dennis R. Carter, PH.D. and Christopher R. Jacobs. PH.D., The Periosteum as a Cellular Source for Functional Tissue Engineering, Tissue Engineering: Part A vol. 15, No. 9, ® Mary Ann Liebert, Inc. DOI: 10.1089/ten.tea.2008.0244, 6 pages.
The Orthopaedic Clinic, Memphis, Tenn, HEALIO, Orthopedicstoday®, The Use of a Periosteal Replacement Membrane for Bone Graft Containment at Allograft-Host Junctions After Tumor Resection and Reconstruction With Bulk Allograft, May 1, 2003, Abstract, 5 pages.

* cited by examiner

*Primary Examiner* — Julie Wu
*Assistant Examiner* — Douglas F White

(57) ABSTRACT

Methods of making and osteoinductive compositions are provided. The method includes mixing isolated periosteum tissue with a demineralized bone matrix to form the osteoinductive composition. The periosteum tissue is isolated from the surface of large bones such as femur, tibia, humerus or a mixture thereof. The demineralized bone matrix can include a plurality of surface demineralized or fully demineralized bone fibers, bone chips, bone particles or mixtures thereof. In the osteoinductive composition the substantially isolated periosteum tissue is from about 0.5% wt. to about 10% wt. A method for repairing a bone defect is also provided. The method of treatment includes applying to the bone defect a substantially effective amount of a mixture of isolated periosteum tissue and demineralized bone matrix.

13 Claims, No Drawings

DEMINERALIZED BONE MATRIX WITH IMPROVED OSTEOINDUCTIVITY

BACKGROUND

The rapid and effective repair of bone defects caused by injury, disease, wounds, or surgery is a goal of orthopedic surgery. Toward this end, a number of bone implants have been used or proposed for use in the repair of bone defects. The biological, physical, and mechanical properties of the bone implants are among the major factors influencing their suitability and performance in various orthopedic applications.

Bone implants are used to repair bone that has been damaged by disease, trauma, or surgery. Bone implants may be utilized when healing is impaired in the presence of certain drugs or in disease states such as diabetes, when a large amount of bone or disc material is removed during surgery, or when bone fusion is needed to create stability. In some types of spinal fusion, for example, bone implants are used to replace the cushioning disc material between the vertebrae or to repair a degenerative facet joint.

Mammalian bone tissue is known to contain one or more proteinaceous materials, presumably active during growth and natural bone healing that can induce a developmental cascade of cellular events resulting in endochondral bone formation. Various factors are present in bone. These include bone morphogenetic or morphogenic proteins (BMPs), bone inductive proteins, bone growth or growth factors, osteogenic proteins, or osteoinductive proteins. While these factors have different effects and functions, as discussed herein, these will be referred to collectively herein as osteoinductive factors.

Autologous cancellous bone ("ACB") long has been considered the gold standard for bone grafts. ACB includes osteogenic cells, which have the potential to assist in bone healing, is nonimmunogenic, and has structural and functional characteristics that should be appropriate for a healthy recipient. Some people do not have adequate amounts of ACB for harvesting. These people include, for example, older people and people who have had previous surgeries. A majority of people however do have adequate amounts of ACB for harvesting. There may nevertheless be reluctance to harvest bone from these people because of pain at the harvest site and potential donor site morbidity.

Conventionally, bone tissue regeneration is achieved by filling a bone repair site with a bone graft. Over time, the bone graft is incorporated by the host and new bone remodels the bone graft. In order to place the bone graft, it is common to use a monolithic bone graft or to form an osteoimplant comprising particulated bone in a carrier. The carrier is thus chosen to be biocompatible, to be resorbable, and to have release characteristics such that the bone graft is accessible.

Bone-related disorders are characterized by bone loss resulting from an imbalance between bone resorption and bone formation. Throughout life, there is a constant remodeling of skeletal bone. In this remodeling process, there is a delicate balance between bone resorption by osteoclasts and subsequent restoration by osteoblasts. Osteoblasts, involved in both endochondral and intramembraneous ossification, are the specialized cells in bone tissue that make matrix proteins resulting in the formation of new bone. Bone formation (e.g., osteogenesis) is essential for the maintenance of bone mass in the skeleton. Unlike osteoblasts, osteoclasts are associated with bone resorption and removal. In normal bone, the balance between osteoblast-mediated bone formation and osteoclast-mediated bone resorption is maintained through complex regulated interactions.

It is known that bone contains osteoinductive factors. These osteoinductive factors are present within the compound structure of cortical bone and are present at very low concentrations, for example, 0.003%. Osteoinductive factors direct the differentiation of pluripotent mesenchymal cells into osteoprogenitor cells that form osteoblasts. Proper demineralization of cortical bone exposes the osteoinductive factors, rendering it osteoinductive.

Bone grafting is used to repair bone voids that are extremely complex, pose a significant health risk to the patient, or fail to heal properly. This is done with materials either from the patient's own body or by using an artificial, synthetic, or natural substitute. Demineralized bone matrix (DBM) based materials are commonly used in these procedures to substitute for, or extend the volume of, autograft and local bone. Thus, demineralized bone matrix implants have been reported to be particularly useful. Demineralized bone matrix is typically derived from cadavers. The bone is removed aseptically and/or treated to kill any infectious agents. The bone is then particulated by milling, mincing or grinding and then the mineral components are extracted for example, by soaking the bone in an acidic solution.

Some DBM formulations have various drawbacks. For example, while the collagen-based matrix of DBM is relatively stable, the active factors within the DBM matrix often can be rapidly degraded within 24 hours after implantation, and in some instances the osteogenic activity can be inactivated within 6 hours after implantation. Therefore, the active factors associated with the DBM may only be available to recruit cells to the site of injury for a short period of time after implantation. For much of the healing process, which may take weeks to months, the implanted DBM material may provide little or no assistance in recruiting cells.

Periosteum tissue is one tissue type that is involved early during normal bone fracture repair process and can recruit various cell types (e.g., mesenchymal stem cells) and bone growth factors necessary for bone fracture repair. Currently, periosteum tissue is discarded during the manufacture of allograft material.

It would, therefore, be useful to develop methods and compositions for increasing bone formation by using periosteum tissue as a source of mesenchymal stem cells and/or growth factors in a demineralized bone composition.

SUMMARY

Methods and compositions are provided that enhance the osteoinductivity of a demineralized bone composition. Accordingly, the present application enhances the osteoinductivity of DBM by the addition of periosteum tissue to the DBM. Periosteum tissue can recruit various cell types (e.g., mesenchymal stem cells) and bone growth factors necessary for bone fracture repair. By including periosteum tissue in the DBM composition, its osteoinductivity is enhanced.

In various embodiments, this application provides an osteoinductive composition comprising substantially isolated periosteum tissue in a demineralized bone matrix. The substantially isolated peiosteum tissue can be in particle, powder and/or fiber form. In various embodiments, the amount of substantially isolated periosteum tissue can be from about 0.5% by weight to about 10% by weight based on the total weight of the osteoinductive composition. In some aspects, the osteoinductive composition of this application can comprise an allograft, syngraft or xenograft.

In various embodiments, the DBM useful for the composition of this application comprises a plurality of surface demineralized bone fibers, bone chips, bone particles or mixtures thereof. Other osteoinductive and osteopromotive additives can be added to the DBM composition of this application, such as for example, bone marrow, blood, a blood product, bone morphogenetic proteins, growth factors and mixtures thereof. The osteoinductive composition of the current application can also comprise calcium phosphate, calcium sulfate, silicon containing ceramic, collagen, collagen derivatives, naturally derived allogenic bone, bone mineral, naturally derived autogenic bone mineral, fully demineralized bone material or mixtures thereof.

In various embodiments, this application also provides a method of repairing a bone defect. The method of repairing provided herein comprises applying to a bone defect a substantially effective amount of a mixture of isolated periosteum tissue and DBM.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present application. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical are as precise as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, for example, 5.5 to 10.

Additionally, unless defined otherwise or apparent from context, all technical and scientific terms used herein have the same meanings as commonly understood by one of ordinary skill in the art to which this invention belongs.

Unless explicitly stated or apparent from context, the following terms are phrases have the definitions provided below:

Definitions

It is noted that, as used in this specification and the appended claims, the singular forms "a," "an," and "the," include plural referents unless expressly and unequivocally limited to one referent. Thus, for example, reference to "a matrix" includes one, two, three or more matrices.

"Allograft," as used herein, refers to a graft of tissue obtained from a donor of the same species as, but with a different genetic make-up from, the recipient, as a tissue transplant between two humans.

"Bioactive agent or bioactive compound," as used herein, refers to a compound or entity that alters, inhibits, activates, or otherwise affects biological or chemical events. For example, bioactive agents may include, but are not limited to, osteogenic or chondrogenic proteins or peptides, anti-AIDS therapeutic agents, anti-cancer therapeutic agents, antibiotics, immunosuppressants, anti-viral therapeutic agents, enzyme inhibitors, hormones, neurotoxins, opioids, hypnotics, anti-histamines, lubricants, tranquilizers, anti-convulsants, muscle relaxants and anti-Parkinson therapeutic agents, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and antiadhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, angiogenic factors, anti-secretory factors, anticoagulants and/or antithrombotic agents, local anesthetics, ophthalmics, prostaglandins, anti-depressants, anti-psychotic therapeutic agents, anti-emetics, and imaging agents. In certain embodiments, the bioactive agent is a drug. Bioactive agents further include RNAs, such as siRNA, and osteoclast stimulating factors. In some embodiments, the bioactive agent may be a factor that stops, removes, or reduces the activity of bone growth inhibitors. In some embodiments, the bioactive agent is a growth factor, cytokine, extracellular matrix molecule or a fragment or derivative thereof, for example, a cell attachment sequence such as RGD. A more complete listing of bioactive agents and specific drugs suitable for use in the present invention may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", Edited by Susan Budavari et al., CRC Press, 1996; and the United States Pharmacopeia-25/National Formulary-20, published by the United States Pharmcopeial Convention, Inc., Rockville Md., 2001, each of which is incorporated herein by reference.

"Biocompatible" means that the matrix will not cause substantial tissue irritation or necrosis at the target tissue site. The term "biocompatible," as used herein, is intended to describe materials that, upon administration in vivo, do not induce undesirable long term effects.

"Biodegradable," as used herein, includes that all or parts of the implant will degrade over time by the action of enzymes, by hydrolytic action and/or by other similar mechanisms in the human body. In various embodiments, "biodegradable" includes that the implant can break down or degrade within the body to non-toxic components after or while a therapeutic agent has been or is being released. By "bioerodible" it is meant that the carrier and/or implant will erode or degrade over time due, at least in part, to contact with substances found in the surrounding tissue, fluids or by cellular action. By "bioabsorbable" or "bioresorbable" it is meant that the carrier and/or implant will be broken down and absorbed within the human body, for example, by a cell or tissue.

"Bone," as used herein, refers to bone that is cortical, cancellous or cortico-cancellous of autogenous, allogenic, xenogenic, or transgenic origin.

"Demineralized," as used herein, refers to any material generated by removing mineral material from tissue, for example, bone tissue. In certain embodiments, the demineralized compositions described herein include preparations containing less than 5% calcium and preferably less than 1% calcium by weight. Partially demineralized bone (e.g., preparations with greater than 5% calcium by weight but containing less than 100% of the original starting amount of calcium) is also considered within the scope of the invention. In some embodiments, demineralized bone has less than 95% of its original mineral content. Demineralized is intended to encompass such expressions as "substantially demineralized," "partially demineralized," and "fully demineralized."

"Demineralized bone matrix," or "DBM" as used herein, refers to any material generated by removing mineral material from bone tissue. In preferred embodiments, the DBM compositions as used herein include preparations containing less than 5% calcium and preferably less than 1% calcium by weight. Partially demineralized bone (for example, preparations with greater than 5% calcium by weight but containing less than 100% of the original starting amount of calcium) are also considered within the scope of the invention.

"Mineralized" as used herein, refers to bone that has been subjected to a process that caused a decrease in their original organic content (e.g., de-fatting, de-greasing). Such a process can result in an increase in the relative inorganic mineral content of the bone. Mineralization may also refer to the mineralization of a matrix such as extracellular matrix or demineralized bone matrix. The mineralization process may take place either in vivo or in vitro.

"Superficially demineralized," as used herein, refers to bone-derived elements possessing at least about 90 weight percent of their original inorganic mineral content, the expression "partially demineralized" as used herein refers to bone-derived elements possessing from about 8 to about 90 weight percent of their original inorganic mineral content and the expression "fully demineralized" as used herein refers to bone containing less than 8% of its original mineral context.

"Mammal," as used herein, refers to organisms from the taxonomy class "mammalian," including but not limited to humans, other primates such as chimpanzees, apes, orangutans and monkeys, rats, mice, cats, dogs, cows, horses, etc.

"Patient," as used herein, refers to a biological system to which a treatment can be administered. A biological system can include, for example, an individual cell, a set of cells (e.g., a cell culture), an organ, or a tissue. Additionally, the term "patient" can refer to animals, including, without limitation, humans.

"A therapeutically effective amount" or "effective amount" is such that when administered, the implant results in alteration of the biological activity, such as, for example, promotion of bone, cartilage and/or other tissue growth, inhibition of inflammation, or reduction or alleviation of pain. In some embodiments the implant is designed for immediate release. In other embodiments the implant is designed for sustained release. In other embodiments, the implant comprises one or more immediate release surfaces and one or more sustained release surfaces.

"Treating" and "treatment" when used in connection with a disease or condition refer to executing a protocol that may include a bone repair procedure, where the bone implant and/or one or more drugs are administered to a patient (human, other normal or otherwise or other mammal), in an effort to alleviate signs or symptoms of the disease or condition or immunological response. Alleviation can occur prior to signs or symptoms of the disease or condition appearing, as well as after their appearance. Thus, treating or treatment includes preventing or prevention of disease or undesirable condition. In addition, treating, treatment, preventing or prevention does not require complete alleviation of signs or symptoms, does not require a cure, and specifically includes protocols that have only a marginal effect on the patient.

"Osteoinduction," as used herein, refers to the ability to stimulate the proliferation and differentiation of pluripotent mesenchymal stem cells (MSCs). In endochondral bone formation, stem cells differentiate into chondroblasts and chondrocytes, laying down a cartilaginous ECM, which subsequently calcifies and is remodeled into lamellar bone. In intramembranous bone formation, the stem cells differentiate directly into osteoblasts, which form bone through direct mechanisms. Osteoinduction can be stimulated by osteogenic growth factors, although some ECM proteins can also drive progenitor cells toward the osteogenic phenotype.

"Osteoconduction," as used herein, refers to the ability to stimulate the attachment, migration, and distribution of vascular and osteogenic cells within the graft material. The physical characteristics that affect the graft's osteoconductive activity include porosity, pore size, and three-dimensional architecture. In addition, direct biochemical interactions between matrix proteins and cell surface receptors play a major role in the host's response to the graft material.

"Osteoconductive," as used herein, refers to the ability of a non-osteoinductive therapeutic agent to serve as a suitable template or therapeutic agent along which bone may grow.

"Osteoimplant," as used herein, refers to any bone-derived implant prepared in accordance with the embodiments of this invention and therefore is intended to include expressions such as bone membrane, bone graft.

"Osteoinductive," as used herein, refers to the quality of being able to recruit cells from the host that have the potential to stimulate new bone formation. Any material that can induce the formation of ectopic bone in the soft tissue of an animal is considered osteoinductive. For example, most osteoinductive materials induce bone formation in athymic rats when assayed according to the method of Edwards et al., "Osteoinduction of Human Demineralized Bone: Characterization in a Rat Model," Clinical Orthopaedics & Rel. Res., 357:219-228, December 1998, incorporated herein by reference. In other instances, osteoinduction is considered to occur through cellular recruitment and induction of the recruited cells to an osteogenic phenotype. Osteoinductivity score refers to a score ranging from 0 to 4 as determined according to the method of Edwards et al. (1998) or an equivalent calibrated test. In the method of Edwards et al., a score of "0" represents no new bone formation; "1" represents 1%-25% of implant involved in new bone formation; "2" represents 26-50% of implant involved in new bone formation; "3" represents 51%-75% of implant involved in new bone formation; and "4" represents >75% of implant involved in new bone formation. In most instances, the score is assessed 28 days after implantation. However, the osteoinductivity score may be obtained at earlier time points such as 7, 14, or 21 days following implantation. Percentage of osteoinductivity refers to an osteoinductivity score at a given time point expressed as a percentage of activity, of a specified reference score. Enhanced osteoinduction includes increases in osteoinduction by using periosteum tissue or cells in the DBM composition. Increases include 10, 15, 20, 25, 30, 35, 40, 45, 50, 55, 60, 65, 70, 75, 80, 85, 90, 95, 96, 97, 98 or 100% or higher increases in osteoinduction as compared to DBM compositions that do not have the periosteum tissue or cells in the composition.

"Osteogenic," as used herein refers to the ability of a graft material to produce bone independently. To have direct osteogenic activity, the graft must contain cellular components that directly induce bone formation. For example, an allograft seeded with activated MSCs would have the potential to induce bone formation directly, without recruitment and activation of host MSC populations. Because many osteoconductive allografts also have the ability to bind and deliver bioactive molecules, their osteoinductive potential will be greatly enhanced.

"Osteopromotive," as used herein, refers describes a material that promotes the de novo formation of bone. Osteopromotive material has the ability to enhance natural bone formation by stimulatory signals. By itself, the material does not have the capacity to induce new bone formation at nonskeletal sites. An example of an osteopromotive material is platelet rich plasma.

"Implantable," as used herein, refers to a biocompatible device (e.g., fiber) retaining potential for successful placement within a mammal. The expression "implantable device" and expressions of the like import as utilized herein refers to an object implantable through surgery, injection, or other suitable means whose primary function is achieved either through its physical presence or mechanical properties.

"Syngraft," as used herein, refers to tissue or organs obtained from a donor who is genetically identical to the recipient "Xenograft," as used herein, refers to tissue or organs from an individual of one species transplanted into or grafted onto an organism of another species, genus, or family.

The headings below are not meant to limit the disclosure in any way; embodiments under any one heading may be used in conjunction with embodiments under any other heading.

Periosteum Tissue

Periosteum is a dense connective membrane that covers and attaches tightly to the outer surface of all bones except the joints of long bones. Periosteum is attached to bone by strong collagenous fibers forming a thin but tough membrane. Generally, the periosteum is thought to contain two layers, an outer fibrous layer and an inner layer called cambium. The outer layer contains fibroblast, blood vessels, nerve fibers, collagen fibers. The cambium contains progenitor cells which are capable of differentiating into chondrogenic and osteoblastic cells. Periosteum attaches to bone by Sharpey's fibers which are strong collagenous fibers. The bone periosteum tissue is the site of early bone formation during fracture repair. A rich source of osteoinductive cells and growth factors, periosteum tissue can now be harvested, and upon adding to a DBM, the periosteum tissue can form an osteoinductive composition having improved bone forming ability and osteoinductive potency useful in repairing a variety of bone defects.

In some embodiments, periosteum tissue can be harvested from all bone surfaces. In other aspects the surface of mammalian large bones such as femur, tibia, humerous or a mixture thereof can be a source of periosteum tissue. The periosteum tissue can be mechanically peeled off by scraping or peeling as thin sheets. Once harvested, the periosteum tissue can be cut up in smaller pieces, ground, placed in an acid or chemical bath prior to mixing with demineralized bone matrix. In other aspects, the mechanically removed periosteum tissue is placed in a buffered solution, shred or ground into particulates and then mixed with DBM. In other aspects, the particulates of periosteum tissue can be further freeze dried, reconstituted and then mixed with DBM.

Periosteum differentiates based on the type of tissue or bone substrate onto which it is implanted; long bone appears to be better for inducing growth of bone. The combination of periosteum tissue and/or cells in the DBM matrix is particularly osteoinductive.

Periosteum can be isolated by surgical removal of the tissue from the bone. In some embodiments, the periosteum is removed from bone using sharp periosteal elevators. Care can be taken to ensure that the cambium layer is removed as well. Confirmation of harvest can be accomplished by frozen or conventional histology. The periosteum can be digested using an enzyme, for example, collagenase or trypsin to isolate the periosteum tissue and or cells, which can be added to the DBM composition.

In some embodiments, the periosteum tissue, once isolated, can be free from materials used in the isolation and identification of the periosteum, such as, for example, enzymes, reagents, prions, viruses, and/or bacteria that may cause disease, inflammatory and/or immunological reactions. In various embodiments, the periosteum tissue is at least 90% free, preferably at least 95% free and, more preferably, at least 99.9 or 100% free of such materials. In some embodiments, the periosteum tissue is at least 90, 91, 92, 93, 94, 95, 96, 97, 98, 99 and/or 100% free.

In various embodiments, the amount of periosteum tissue present in the composition resulting from mixing it with DBM is from about 0.5% by weight to about 10% by weight based on the total weight of the osteoinductive composition. In some embodiments, the amount of periosteum tissue present in the composition resulting from mixing it with DBM is from about 0.1, 0.2, 0.3, 0.4, 0.5%, 0.75, 1.0, 1.25, 1.50, 1.75, 2.0, 2.25, 2.50, 2.75, 3.0, 3.25, 3.50, 3.75, 4.0, 4.25, 4.50, 4.75, 5.0, 5.25, 5.50, 5.75, 6.0, 6.25, 6.50, 6.75, 7.0, 7.25, 7.50, 7.75, 8.0, 8.25, 8.50, 8.75, 9.0, 9.25, 9.50, 9.75 to about 10% by weight based on the total weight of the osteoinductive composition.

In other embodiments, prior to mixing with DBM, the periosteum tissue is subjected to terminal sterilization or an aseptic process to prevent microbial growth according to processes well known in the art. In yet other embodiments, the mixture of periosteum tissue fibers and/or particles and DBM is subjected to terminal sterilization or an aseptic process. Terminal sterilization can be accomplished by known techniques such as exposure to gamma radiation and ethylene oxide.

In some embodiments, in order to adhere the periosteum tissue fibers and/or particles to DBM, the mixture of periosteum fibers and/or particles and DBM can be further subjected to treatment with chemicals, air drying, freeze drying or heating.

Demineralized Bone

DBM may be prepared in any suitable manner. In one embodiment, the DBM is prepared through the acid extraction of minerals from bone, bone fibers, bone chips, bone particles or mixtures thereof. It includes the collagen matrix of the bone together with acid insoluble proteins including bone morphogenic proteins (BMPs) and other growth factors. It can be formulated for use as granules, gels, sponge material or putty and can be freeze-dried for storage. Sterilization procedures used to protect from disease transmission may reduce the activity of beneficial growth factors in the DBM. DBM provides an initial osteoconductive matrix and exhibits a degree of osteoinductive potential, inducing the infiltration and differentiation of osteoprogenitor cells from the surrounding tissues.

DBM preparations have been used for many years in orthopedic medicine to promote the formation of bone. For example, DBM has found use in the repair of fractures, in the fusion of vertebrae, in joint replacement surgery, and in treating bone destruction due to underlying disease such as rheumatoid arthritis. DBM is thought to promote bone formation in vivo by osteoconductive and osteoinductive processes. The osteoinductive effect of implanted DBM compositions is thought to result from the presence of active growth factors present on the isolated collagen-based matrix. These factors include members of the TGF-β, IGF, and BMP protein families. Particular examples of osteoinductive factors include TGF-β, IGF-1, IGF-2, BMP-2, BMP-7, parathyroid hormone (PTH), and angiogenic factors. Other osteoinductive factors such as osteocalcin and osteopontin are also likely to be present in DBM preparations as well. There are also likely to be other unnamed or undiscovered osteoinductive factors present in DBM.

In one demineralization procedure, the bone is subjected to an acid demineralization step followed by a defatting/disinfecting step. The bone, bone fibers, bone chips, bone particles or mixtures thereof are immersed in acid to effect demineralization. Acids that can be employed in this step include inorganic acids such as hydrochloric acid and as well as organic acids such as formic acid, acetic acid, peracetic acid, citric acid, propionic acid, and the like. The depth of demineralization into the bone surface can be controlled by adjusting the treatment time, temperature of the demineralizing solution, concentration of the demineralizing solution, and agitation intensity during treatment. Thus, in various embodiments, the DBM may be fully demineralized, partially demineralized, or surface demineralized.

The demineralized bone is rinsed with sterile water and/or buffered solution(s) to remove residual amounts of acid and thereby raise the pH. A suitable defatting/disinfectant solution is an aqueous solution of ethanol, the ethanol being a good solvent for lipids and the water being a good hydrophilic carrier to enable the solution to penetrate more deeply into the bone particles. The aqueous ethanol solution also disinfects the bone by killing vegetative microorganisms and viruses. Ordinarily, at least about 10 to 40 percent by weight of water (i.e., about 60 to 90 weight percent of defatting agent such as alcohol) is present in the defatting disinfecting solution to produce optimal lipid removal and disinfection within a given period of time. A suitable concentration range of the defatting solution is from about 60 to about 85 weight percent alcohol, or about 70 weight percent alcohol. In some embodiments, a suitable concentration of the defatting solution is from about 60, 61, 62, 63, 64, 65, 66, 67, 68, 69, 70, 71, 72, 73, 74, 75, 76, 77, 78, 79, 80, 81, 82, 83, 84 to about 85 weight percent alcohol.

In some embodiments, the demineralized bone may be further treated to effect properties of the bone. For example, the DBM may be treated to disrupt the collagen structure of the DBM. Such treatment may comprise collagenase treatment, heat treatment, mechanical treatment, or other.

Carrier for DBM

Generally, materials for the carrier may be biocompatible in vivo and optionally biodegradable. In some uses, the carrier acts as a temporary scaffold until replaced completely by new bone. Suitable carriers can be any number of compounds and/or polymers, such as polymer sugars, proteins, long chain hydrophilic block copolymers, reverse phase block copolymers, hyaluronic acid, polyuronic acid, mucopolysaccharide, proteoglycan, polyoxyethylene, surfactants, including the pluronics series of nonionic surfactants, and peptide thickener. Suggested classes of biocompatible fluid carrier would include polyhydroxy compound, polyhydroxy ester, fatty alcohol, fatty alcohol ester, fatty acid, fatty acid ester, liquid silicone, mixtures thereof, and the like. Settable materials may be used, and they may set up either in situ, or prior to implantation. The bone fibers and carrier (or delivery or support system) together form an osteoimplant useful in clinical applications.

Examples of suitable biocompatible fluid carrier include, but are not limited to:

(i) Polyhydroxy compound, for example, such classes of compounds as the acyclic polyhydric alcohols, non-reducing sugars, sugar alcohols, sugar acids, monosaccarides, disaccharides, water-soluble or water dispersible oligosaccharides, polysaccharides and known derivatives of the foregoing. Specific polyhydroxy compounds include, 1,2-propanediol, glycerol, 1,4,-butylene glycol trimethylolethane, trimethylolpropane, erythritol, pentaerythritol, ethylene glycols, diethylene glycol, triethylene glycol, tetraethylene glycol, propylene glycol, dipropylene glycol; polyoxyethylene-polyoxypropylene copolymer, for example, of the type known and commercially available under the trade names Pluronic and Emkalyx; polyoxyethylene-polyoxypropylene block copolymer, for example, of the type known and commercially available under the trade name Poloxamer; alkylphenolhydroxypolyoxyethylene, for example, of the type known and commercially available under the trade name Triton, polyoxyalkylene glycols such as the polyethylene glycols, xylitol, sorbitol, mannitol, dulcitol, arabinose, xylose, ribose, adonitol, arabitol, inositol, fructose, galactose, glucose, mannose, sorbose, sucrose, maltose, lactose, maltitol, lactitol, stachyose, maltopentaose, cyclomaltohexaose, carrageenan, agar, dextran, alginic acid, guar gum, gum tragacanth, locust bean gum, gum arabic, xanthan gum, amylose, mixtures of any of the foregoing, and the like.

(ii) Polyhydroxy ester, for example, liquid and solid monoesters and diesters of glycerol can be used to good effect, the solid esters being dissolved up in a suitable vehicle, for example, propylene glycol, glycerol, polyethylene glycol of 200-1000 molecular weight. Liquid glycerol esters include monacetin and diacetin and solid glycerol esters include such fatty acid monoesters of glycerol as glycerol monolaurate, glyceryl monopalmitate, glyceryl monostearate. In various embodiments, the carrier herein comprises glyceryl monolaurate dissolved in glycerol or a 4:1 to 1:4 weight mixtures of glycerol and propylene glycol, poly (oxyalkylene) glycol ester, and the like.

(iii) Fatty alcohol, for example primary alcohols, usually straight chain having from 6 to 13 carbon atoms, including caproic alcohol, caprylic alcohol, undecyl alcohol, lauryl alcohol, and tridecanol.

(iv) Fatty alcohol ester, for example, ethyl hexyl palmitate, isodecyl neopentate, octadodecyl benzoate, diethyl hexyl maleate, and the like.

(v) Fatty acid having from 6 to 11 carbon atoms, for example, hexanoic acid, heptanoic acid, octanoic acid, decanoic acid and undecanoic acid.

(vi) Fatty acid ester, for example, polyoxyethylene-sorbitan-fatty acid esters, for example, mono- and tri-lauryl, palmityl, stearyl, and oleyl esters including of the type available under the trade name Tween from Imperial Chemical Industries; polyoxyethylene fatty acid esters including polyoxyethylene stearic acid esters of the type known and commercially available under the trade name Myrj; propylene glycol mono- and di-fatty acid esters such as propylene glycol dicaprylate; propylene glycol dilaurate, propylene glycol hydroxy stearate, propylene glycol isostearate, propylene glycol laureate, propylene glycol ricinoleate, propylene glycol stearate, and propylene glycol caprylic-capric acid diester available under the trade name Miglyol; mono-, di-, and mono/di-glycerides, such as the esterification products of caprylic or caproic acid with glycerol, for example, of the type known and commercially available under the trade name Imwitor; sorbitan fatty acid esters, or of the type known and commercially available under the trade name Span, including sorbitan-monolauryl,-monopalmityl, -monostearyl, -tristearyl, -monooleyl and triolcylesters; monoglycerides, for example, glycerol monooleate, glycerol monopalmitate and glycerol monostearate, for example as known and commercially available under the trade names Myvatex, Myvaplex and Myverol, and acetylated, for example, mono- and di-acetylated monoglycerides, for example, as known and commercially available under the trade name Myvacet; isobutyl tallowate, n-butylstearate, n-butyl oleate, and n-propyl oleate.

(vii) Liquid silicone, for example, polyalkyl siloxanes such as polymethyl siloxane and poly (dimethyl siloxane) and polyalkyl arylsiloxane.

Additives

In various embodiments, the DBM provided herein may be used with growth factors, extracts, peptide hormones, or other additives to increase the osteoinductive capacity of the DBM or to impart other benefits to the DBM. It will be appreciated that the amount of additive used will vary depending upon the type of additive, the specific activity of the particular additive preparation employed, and the intended use of the composition. The desired amount can be readily determinable by the user.

In some embodiments, a growth factor and/or therapeutic agent may be disposed on or in the DBM by hand, electrospraying, ionization spraying or impregnating, vibratory dispersion (including sonication), nozzle spraying, compressed-air-assisted spraying, brushing and/or pouring. For example, a growth factor such as rhBMP-2 may be disposed on or in the DBM by the surgeon before the DBM is administered or it may be available from the manufacturer beforehand.

The DBM may comprise at least one growth factor. These growth factors include osteoinductive agents (e.g., agents that cause new bone growth in an area where there was none) and/or osteoconductive agents (e.g., agents that cause in growth of cells into and/or through the DBM). Osteoinductive agents can be polypeptides or polynucleotides compositions. Polynucleotide compositions of the osteoinductive agents include, but are not limited to, isolated Bone Morphogenetic Protein (BMP), Vascular Endothelial Growth Factor (VEGF), Connective Tissue Growth Factor (CTGF), Osteoprotegerin, Growth Differentiation Factors (GDFs), Cartilage Derived Morphogenic Proteins (CDMPs), LIM Mineralization Proteins (LMPs), Platelet derived growth factor, (PDGF or rhPDGF), Insulin-like growth factor (IGF) or Transforming Growth Factor beta (TGF-beta) polynucleotides. Polynucleotide compositions of the osteoinductive agents include, but are not limited to, gene therapy vectors harboring polynucleotides encoding the osteoinductive polypeptide of interest. Gene therapy methods often utilize a polynucleotide, which codes for the osteoinductive polypeptide operatively linked or associated to a promoter or any other genetic elements necessary for the expression of the osteoinductive polypeptide by the target tissue. Such gene therapy and delivery techniques are known in the art (See, for example, International Publication No. WO90/11092, the disclosure of which is herein incorporated by reference in its entirety). Suitable gene therapy vectors include, but are not limited to, gene therapy vectors that do not integrate into the host genome. Alternatively, suitable gene therapy vectors include, but are not limited to, gene therapy vectors that integrate into the host genome.

In some embodiments, the polynucleotide is delivered in plasmid formulations. Plasmid DNA or RNA formulations refer to polynucleotide sequences encoding osteoinductive polypeptides that are free from any delivery vehicle that acts to assist, promote or facilitate entry into the cell, including viral sequences, viral particles, liposome formulations, lipofectin, precipitating agents or the like. Optionally, gene therapy compositions can be delivered in liposome formulations and lipofectin formulations, which can be prepared by methods well known to those skilled in the art. General methods are described, for example, in U.S. Pat. Nos. 5,593,972, 5,589,466, and 5,580,859, the disclosures of which are herein incorporated by reference in their entireties.

Gene therapy vectors further comprise suitable adenoviral vectors including, but not limited to for example, those described in U.S. Pat. No. 5,652,224, which is herein incorporated by reference.

Polypeptide compositions of the isolated osteoinductive agents include, but are not limited to, isolated Bone Morphogenetic Protein (BMP), Vascular Endothelial Growth Factor (VEGF), Connective Tissue Growth Factor (CTGF), Osteoprotegerin, Growth Differentiation Factors (GDFs), Cartilage Derived Morphogenic Proteins (CDMPs), Lim Mineralization Proteins (LMPs), Platelet derived growth factor, (PDGF or rhPDGF), Insulin-like growth factor (IGF) or Transforming Growth Factor beta (TGF-beta707) polypeptides. Polypeptide compositions of the osteoinductive agents include, but are not limited to, full length proteins, fragments or variants thereof.

Variants of the isolated osteoinductive agents include, but are not limited to, polypeptide variants that are designed to increase the duration of activity of the osteoinductive agent in vivo. Preferred embodiments of variant osteoinductive agents include, but are not limited to, full length proteins or fragments thereof that are conjugated to polyethylene glycol (PEG) moieties to increase their half-life in vivo (also known as pegylation). Methods of pegylating polypeptides are well known in the art (See, e.g., U.S. Pat. No. 6,552,170 and European Pat. No. 0,401,384 as examples of methods of generating pegylated polypeptides). In some embodiments, the isolated osteoinductive agent(s) are provided as fusion proteins. In one embodiment, the osteoinductive agent(s) are available as fusion proteins with the Fc portion of human IgG. In another embodiment, the osteoinductive agent(s) are available as hetero- or homodimers or multimers. Examples of some fusion proteins include, but are not limited to, ligand fusions between mature osteoinductive polypeptides and the Fc portion of human Immunoglobulin G (IgG). Methods of making fusion proteins and constructs encoding the same are well known in the art.

Isolated osteoinductive agents that are included within carrier are typically sterile. In a non-limiting method, sterility is readily accomplished for example by filtration through sterile filtration membranes (e.g., 0.2 micron membranes or filters). In one embodiment, the isolated osteoinductive agents include one or more members of the family of Bone Morphogenetic Proteins ("BMPs"). BMPs are a class of proteins thought to have osteoinductive or growth-promoting activities on endogenous bone tissue, or function as pro-collagen precursors. Known members of the BMP family include, but are not limited to, BMP-1, BMP-2, BMP-3, BMP-4, BMP-5, BMP-6, BMP-7, BMP-8, BMP-9, BMP-10, BMP-11, BMP-12, BMP-13, BMP-15, BMP-16, BMP-17, BMP-18 as well as polynucleotides or polypeptides thereof, as well as mature polypeptides or polynucleotides encoding the same.

BMPs utilized as osteoinductive agents comprise one or more of BMP-1; BMP-2; BMP-3; BMP-4; BMP-5; BMP-6; BMP-7; BMP-8; BMP-9; BMP-10; BMP-11; BMP-12; BMP-13; BMP-15; BMP-16; BMP-17; or BMP-18; as well as any combination of one or more of these BMPs, including full length BMPs or fragments thereof, or combinations thereof, either as polypeptides or polynucleotides encoding the polypeptide fragments of all of the recited BMPs. The isolated BMP osteoinductive agents may be administered as polynucleotides, polypeptides, full length protein or combinations thereof.

In another embodiment, isolated osteoinductive agents include osteoclastogenesis inhibitors to inhibit bone resorption of the bone tissue surrounding the site of implantation by osteoclasts. Osteoclast and osteoclastogenesis inhibitors include, but are not limited to, osteoprotegerin polynucleotides or polypeptides, as well as mature osteoprotegerin proteins, polypeptides or polynucleotides encoding the same. Osteoprotegerin is a member of the TNF-receptor superfamily and is an osteoblast-secreted decoy receptor that functions as a negative regulator of bone resorption. This protein specifically binds to its ligand, osteoprotegerin ligand (TNFSF11/OPGL), both of which are key extracellular regulators of osteoclast development.

Osteoclastogenesis inhibitors further include, but are not limited to, chemical compounds such as bisphosphonate, 5-lipoxygenase inhibitors such as those described in U.S. Pat. Nos. 5,534,524 and 6,455,541 (the contents of which are herein incorporated by reference in their entireties), heterocyclic compounds such as those described in U.S. Pat. No. 5,658,935 (herein incorporated by reference in its entirety), 2,4-dioxoimidazolidine and imidazolidine derivative compounds such as those described in U.S. Pat. Nos. 5,397,796 and 5,554,594 (the contents of which are herein incorporated by reference in their entireties), sulfonamide derivatives such as those described in U.S. Pat. No. 6,313,119 (herein incorporated by reference in its entirety), or acylguanidine compounds such as those described in U.S. Pat. No. 6,492,356 (herein incorporated by reference in its entirety).

In another embodiment, isolated osteoinductive agents include one or more members of the family of Connective Tissue Growth Factors ("CTGFs"). CTGFs are a class of proteins thought to have growth-promoting activities on connective tissues. Known members of the CTGF family include, but are not limited to, CTGF-1, CTGF-2, CTGF-4 polynucleotides or polypeptides thereof, as well as mature proteins, polypeptides or polynucleotides encoding the same.

In another embodiment, isolated osteoinductive agents include one or more members of the family of Vascular Endothelial Growth Factors ("VEGFs"). VEGFs are a class of proteins thought to have growth-promoting activities on vascular tissues. Known members of the VEGF family include, but are not limited to, VEGF-A, VEGF-B, VEGF-C, VEGF-D, VEGF-E or polynucleotides or polypeptides thereof, as well as mature VEGF-A, proteins, polypeptides or polynucleotides encoding the same.

In another embodiment, isolated osteoinductive agents include one or more members of the family of Transforming Growth Factor-beta genes ("TGFbetas"). TGF-betas are a class of proteins thought to have growth-promoting activities on a range of tissues, including connective tissues. Known members of the TGF-beta family include, but are not limited to, TGF-beta-1, TGF-beta-2, TGF-beta-3, polynucleotides or polypeptides thereof, as well as mature protein, polypeptides or polynucleotides encoding the same.

In another embodiment, isolated osteoinductive agents include one or more Growth Differentiation Factors ("GDFs"). Known GDFs include, but are not limited to, GDF-1, GDF-2, GDF-3, GDF-7, GDF-10, GDF-11, and GDF-15. For example, GDFs useful as isolated osteoinductive agents include, but are not limited to, the following GDFs: GDF-1 polynucleotides or polypeptides corresponding to GenBank Accession Numbers M62302, AAA58501, and AAB94786, as well as mature GDF-1 polypeptides or polynucleotides encoding the same. GDF-2 polynucleotides or polypeptides corresponding to GenBank Accession Numbers BC069643, BC074921, Q9UK05, AAH69643, or AAH74921, as well as mature GDF-2 polypeptides or polynucleotides encoding the same. GDF-3 polynucleotides or polypeptides corresponding to GenBank Accession Numbers AF263538, BC030959, AAF91389, AAQ89234, or Q9NR23, as well as mature GDF-3 polypeptides or polynucleotides encoding the same. GDF-7 polynucleotides or polypeptides corresponding to GenBank Accession Numbers AB158468, AF522369, AAP97720, or Q7Z4P5, as well as mature GDF-7 polypeptides or polynucleotides encoding the same. GDF-10 polynucleotides or polypeptides corresponding to GenBank Accession Numbers BC028237 or AAH28237, as well as mature GDF-10 polypeptides or polynucleotides encoding the same.

GDF-11 polynucleotides or polypeptides corresponding to GenBank Accession Numbers AF100907, NP_005802 or O95390, as well as mature GDF-11 polypeptides or polynucleotides encoding the same. GDF-15 polynucleotides or polypeptides corresponding to GenBank Accession Numbers BC008962, BC000529, AAH00529, or NP004855, as well as mature GDF-15 polypeptides or polynucleotides encoding the same.

In another embodiment, isolated osteoinductive agents include Cartilage Derived Morphogenic Protein (CDMP) and Lim Mineralization Protein (LMP) polynucleotides or polypeptides. Known CDMPs and LMPs include, but are not limited to, CDMP-1, CDMP-2, LMP-1, LMP-2, or LMP-3.

CDMPs and LMPs useful as isolated osteoinductive agents include, but are not limited to, the following CDMPs and LMPs: CDMP-1 polynucleotides and polypeptides corresponding to GenBank Accession Numbers NM_000557, U13660, NP_000548 or P43026, as well as mature CDMP-1 polypeptides or polynucleotides encoding the same. CDMP-2 polypeptides corresponding to GenBank Accession Numbers or P55106, as well as mature CDMP-2 polypeptides. LMP-1 polynucleotides or polypeptides corresponding to GenBank Accession Numbers AF345904 or AAK30567, as well as mature LMP-1 polypeptides or polynucleotides encoding the same. LMP-2 polynucleotides or polypeptides corresponding to GenBank Accession Numbers AF345905 or AAK30568, as well as mature LMP-2 polypeptides or polynucleotides encoding the same. LMP-3 polynucleotides or polypeptides corresponding to GenBank Accession Numbers AF345906 or AAK30569, as well as mature LMP-3 polypeptides or polynucleotides encoding the same.

In another embodiment, isolated osteoinductive agents include one or more members of any one of the families of Bone Morphogenetic Proteins (BMPs), Connective Tissue Growth Factors (CTGFs), Vascular Endothelial Growth Factors (VEGFs), Osteoprotegerin or any of the other osteoclastogenesis inhibitors, Growth Differentiation Factors (GDFs), Cartilage Derived Morphogenic Proteins (CDMPs), Lim Mineralization Proteins (LMPs), or Transforming Growth Factor-betas (TGF-betas), TP508 (an angiogenic tissue repair peptide), as well as mixtures or combinations thereof.

In another embodiment, the one or more isolated osteoinductive agents useful in the DBM are selected from the group consisting of BMP-1, BMP-2, BMP-3, BMP-4, BMP-5, BMP-6, BMP-7, BMP-8, BMP-9, BMP-10, BMP-11, BMP-12, BMP-13, BMP-15, BMP-16, BMP-17, BMP-18, or any combination thereof; CTGF-1, CTGF-2, CGTF-3, CTGF-4, or any combination thereof; VEGF-A, VEGF-B, VEGF-C, VEGF-D, VEGF-E, or any combination thereof; GDF-1, GDF-2, GDF-3, GDF-7, GDF-10, GDF-11, GDF-15, or any combination thereof; CDMP-1, CDMP-2, LMP-1, LMP-2, LMP-3, and or combination thereof; osteoprotegerin; TGF-beta-1, TGF-beta-2, TGF-beta-3, or any combination thereof; or any combination of one or more members of these groups.

The concentrations of growth factor can be varied based on the desired length or degree of osteogenic effects desired. Similarly, one of skill in the art will understand that the duration of sustained release of the growth factor can be modified by the manipulation of the compositions comprising the sustained release formulation, such as for example, modifying the percent of DBM found within a sustained release formulation, microencapsulation of the formulation within polymers, including polymers having varying degradation times and characteristics, and layering the formulation in varying thicknesses in one or more degradable polymers. These sustained release formulations can therefore be designed to provide customized time release of growth factors that simulate the natural healing process.

In some embodiments, a statin may be used as the growth factor. Statins include, but is not limited to, atorvastatin, simvastatin, pravastatin, cerivastatin, mevastatin (see U.S. Pat. No. 3,883,140, the entire disclosure is herein incorporated by reference), velostatin (also called synvinolin; see U.S. Pat. Nos. 4,448,784 and 4,450,171 these entire disclosures are herein incorporated by reference), fluvastatin, lovastatin, rosuvastatin and fluindostatin (Sandoz XU-62-320), dalvastain (EP Appln. Publn. No. 738510 A2, the entire disclosure is herein incorporated by reference), eptastatin, pitavastatin, or pharmaceutically acceptable salts thereof or a combination thereof In various embodiments, the statin may comprise mixtures of (+)R and (−)-S enantiomers of the statin. In various embodiments, the statin may comprise a 1:1 racemic mixture of the statin.

The growth factor may contain inactive materials such as buffering agents and pH adjusting agents such as potassium bicarbonate, potassium carbonate, potassium hydroxide, sodium acetate, sodium borate, sodium bicarbonate, sodium carbonate, sodium hydroxide or sodium phosphate; degradation/release modifiers; drug release adjusting agents; emulsifiers; preservatives such as benzalkonium chloride, chlorobutanol, phenylmercuric acetate and phenylmercuric nitrate, sodium bisulfate, sodium bisulfate, sodium thiosulfate, thimerosal, methylparaben, polyvinyl alcohol and phenylethyl alcohol; solubility adjusting agents; stabilizers; and/or cohesion modifiers. In some embodiments, the growth factor may comprise sterile and/or preservative free material.

These above inactive ingredients may have multi-functional purposes including the carrying, stabilizing and controlling the release of the growth factor and/or other therapeutic agent(s). The sustained release process, for example, may be by a solution-diffusion mechanism or it may be governed by an erosion-sustained process.

The amount of growth factor, e.g., bone morphogenic protein may be sufficient to cause bone and/or cartilage growth. In some embodiments, the growth factor is rhBMP-2 and is contained in one or more carriers in an amount of from 0.05 to 2 mg per cubic centimeter of the biodegradable carrier. In some embodiments, the growth factor is rhBMP-2 and is contained in one or more carriers in an amount of from 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.0, 1.05, 1.10, 1.15, 1.20, 1.25, 1.30, 1.35, 1.40, 1.45, 1.50, 1.55, 1.60, 1.65, 1.70, 1.75, 1.80, 1.85, 1.90, 1.95. to 2.0 mg per cubic centimeter of the biodegradable carrier. In some embodiments, the amount of rhBMP-2 morphogenic protein is from 2.0 to 2.5 mg per cubic centimeter (cc) of the biodegradable carrier. In some embodiments, the amount of rhBMP-2 morphogenic protein is from 2.0, 2.05, 2.10, 2.15, 2.20, 2.25, 2.30, 2.35, 2.40, 2.45 to 2.50 mg per cubic centimeter (cc) of the biodegradable carrier.

In some embodiments, the growth factor is supplied in an aqueous buffered solution. Exemplary aqueous buffered solutions include, but are not limited to, TE, HEPES (2-[4-(2-hydroxyethyl)-1-piperazinyl]ethanesulfonic acid), MES (2-morpholino-ethanesulfonic acid), sodium acetate buffer, sodium citrate buffer, sodium phosphate buffer, a Tris buffer (e.g., Tris-HCL), phosphate buffered saline (PBS), sodium phosphate, potassium phosphate, sodium chloride, potassium chloride, glycerol, calcium chloride or a combination thereof. In various embodiments, the buffer concentration can be from about 1 mM to 100 mM.

In some embodiments, the BMP-2 is provided in a vehicle (including a buffer) containing sucrose, glycine, L-glutamic acid, sodium chloride, and/or polysorbate 80.

Additional Therapeutic Agents

In some embodiments, in addition to the growth factor, the DBM may contain other therapeutic agents.

Any of a variety of medically and/or surgically useful optional substances can be incorporated in, or associated with, the osteoinductive factors either before, during, or after preparation of the osteoinductive composition. Thus, for example when demineralized bone particles are used to form the material, one or more of such substances may be introduced into the demineralized bone particles, for example, by soaking or immersing the bone particles in a solution or dispersion of the desired substance(s).

Medically/surgically useful substances that can be readily combined with the DBM include, for example, calcium phosphate, calcium sulfate, silicon containing ceramic, collagen, collagen derivatives, insoluble collagen derivatives, naturally derived allogenic bone mineral, naturally derived autogenic bone mineral, fully mineralized bone material or mixtures thereof Other soluble solids and/or liquids dissolved for combination with the DBM include antiviricides, particularly those effective against HIV and hepatitis; antimicrobials and/or antibiotics such as erythromycin, bacitracin, neomycin, penicillin, polymyxin B, tetracyclines, viomycin, chloromycetin and streptomycins, cefazolin, ampicillin, azactam, tobramycin, clindamycin and gentamicin, etc.; biocidal/biostatic sugars such as dextroal, glucose, etc.; amino acids, peptides, vitamins, inorganic elements, co-factors for protein synthesis; hormones; endocrine tissue or tissue fragments; synthesizers; enzymes such as collagenase, peptidases, oxidases, etc.; polymer cell scaffolds with parenchymal cells; angiogenic drugs and polymeric carriers containing such drugs; collagen lattices; antigenic agents; cytoskeletal agents; cartilage fragments, living cells such as chondrocytes, bone marrow cells, mesenchymal stem cells, natural extracts, tissue transplants, bone, demineralized bone powder, autogenous tissues such blood, serum, soft tissue, bone marrow, etc.; bioadhesives, bone morphogenic proteins (BMPs), angiogenic factors, transforming growth factor (TGF-beta), insulin-like growth factor (IGF-1); growth hormones such as somatotropin; bone digestors; antitumor agents; immuno-suppressants; permeation enhancers, e.g., fatty acid esters such as laureate, myristate and stearate monoesters of polyethylene glycol, enamine derivatives, alpha-keto aldehydes, etc.; and, nucleic acids. The amounts of such optionally added substances can vary widely with optimum levels being readily determined in a specific case by routine experimentation.

In one embodiment, a tissue-derived extract or partially demineralized bone may be added to the demineralized bone matrix. The extract may be derived from any suitable tissue, such as bone, bladder, kidney, brain, skin, or connective tissue. Further, the extract may be derived in any suitable manner. The extract may be allogenic, autogenic, xenogenic, or transgenic. In embodiments wherein the extract is bone-derived, the bone may be cortical, cancellous, or cortico-cancellous and may be demineralized, partially demineralized, or mineralized. In some embodiments, the extract may comprise demineralized bone, partially demineralized bone, mineral derived from bone, or collagen derived from bone. In some embodiments, the tissue-derived extract may be a protein extract.

Bone regeneration involves a multitude of cells (e.g. cartilage, fibroblasts, endothelial, etc.) besides osteoblasts. In various embodiments, stem cells from periosteum tissue may be combined with the DBM. Accordingly, the osteoinductive DBM composition may be used to deliver stem cells, which offers the potential to give rise to different types of cells in the bone repair process. In various embodiments, the additive may comprise radiopaque substances, angiogenesis promoting materials, bioactive agents, osteoinducing agents.

In certain embodiments, the additive is adsorbed to or otherwise associated with the DBM. The additive may be associated with the osteoinductive DBM composition through specific or non-specific interactions, or covalent or noncovalent interactions. Examples of specific interactions include those between a ligand and a receptor, an epitope and an antibody. Examples of nonspecific interactions include hydrophobic interactions, electrostatic interactions, magnetic interactions, dipole interactions, van der Waals interactions, or hydrogen bonding. In certain embodiments, the additive is attached to the osteoinductive DBM composition, for example, to the carrier, using a linker so that the additive is free to associate with its receptor or site of action in vivo. In other embodiments the additive is either covalently or non-covalently attached to the carrier. In certain embodiments, the additive may be attached to a chemical compound such as a peptide that is recognized by the carrier. In another embodiment, the additive is attached to an antibody, or fragment thereof, that recognizes an epitope found within the carrier. In certain embodiments at least additives are attached to the osteoimplant. In other embodiments at least three additives are attached to the osteoinductive composition. An additive may be provided within the osteoinductive composition in a sustained release format. For example, the additive may be encapsulated within biodegradable nanospheres, or microspheres.

Exemplary therapeutic agents include but are not limited to IL-1 inhibitors, such Kineret® (anakinra), which is a recombinant, non-glycosylated form of the human inerleukin-1 receptor antagonist (IL-1Ra), or AMG 108, which is a monoclonal antibody that blocks the action of IL-1. Therapeutic agents also include excitatory amino acids such as glutamate and aspartate, antagonists or inhibitors of glutamate binding to NMDA receptors, AMPA receptors, and/or kainate receptors. Interleukin-1 receptor antagonists, thalidomide (a TNF-α release inhibitor), thalidomide analogues (which reduce TNF-α production by macrophages), quinapril (an inhibitor of angiotensin II, which upregulates TNF-α), interferons such as IL-11 (which modulate TNF-α receptor expression), and aurin-tricarboxylic acid (which inhibits TNF-α), may also be useful as therapeutic agents for reducing inflammation. It is further contemplated that where desirable a pegylated form of the above may be used. Examples of still other therapeutic agents include NF kappa B inhibitors such as antioxidants, such as dilhiocarbamate, and other compounds, such as, for example, sulfasalazine.

Examples of therapeutic agents suitable for use also include, but are not limited to an anti-inflammatory agent, analgesic agent, or osteoinductive growth factor or a combination thereof. Anti-inflammatory agents include, but are not limited to, apazone, celecoxib, diclofenac, diflunisal, enolic acids (piroxicam, meloxicam), etodolac, fenamates (mefenamic acid, meclofenamic acid), gold, ibuprofen, indomethacin, ketoprofen, ketorolac, nabumetone, naproxen, nimesulide, salicylates, sulfasalazine [2-hydroxy-5-[-4-[C2-pyridinylamino)sulfonyl]azo]benzoic acid, sulindac, tepoxalin, and tolmetin; as well as antioxidants, such as dithiocarbamate, steroids, such as cortisol, cortisone, hydrocortisone, fludrocortisone, prednisone, prednisolone, methylprednisolone, triamcinolone, betamethasone, dexamethasone, beclomethasone, fluticasone or a combination thereof.

Suitable analgesic agents include, but are not limited to, acetaminophen, bupivicaine, fluocinolone, lidocaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, mepiridine, methadone, morphine, nalbuphine, opium, oxycodone, papaveretum, pentazocine, pethidine, phenoperidine, piritramide, dextropropoxyphene, remifentanil, tilidine, tramadol, codeine, dihydrocodeine, meptazinol, dezocine, eptazocine, flupirtine, amitriptyline, carbamazepine, gabapentin, pregabalin, or a combination thereof.

Addition of DBM to Carrier

In various embodiments, the DBM provided herein may be combined, with or without additives, with a carrier or excipient to achieve consistency for specific uses. For example, a carrier may be selected to provide the DBM composition in a gel consistency, a putty consistency, a matrix consistency, or other to form an osteoinductive composition. The osteoinductive composition may be configured to be moldable, extrudable, or substantially solid. The osteoinductive composition may be configured to substantially retain its shape in water for a period of time. The osteoinductive composition may form an osteoimplant useful in clinical applications. Suitable carriers may include surface demineralized bone; mineralized bone; nondemineralized cancellous scaffolds; demineralized cancellous scaffolds; cancellous bone chips; bone particles, bone particulates, demineralized, guanidine extracted, species-specific (allogenic) bone; specially treated particulate, protein extracted, demineralized, xenogenic bone; collagen; silicon containing ceramic; synthetic hydroxyapatites; synthetic calcium phosphate materials; tricalcium phosphate, sintered hydroxyapatite, settable hydroxyapatite; polylactide polymers; polyglycolide polymers, polylactide-co-glycolide copolymers; tyrosine polycarbonate; calcium sulfate; collagen sheets; settable calcium phosphate; polymeric cements; settable poly vinyl alcohols, polyurethanes; resorbable polymers; and other large polymers; liquid settable polymers; and other biocompatible settable materials. The carrier may further comprise a polyol (including glycerol or other polyhydroxy compound), a polysaccharide (including starches), a hydrogel (including alginate, chitosan, dextran, pluronics, N,O-carboxymethylchitosan glucosamine (NOCC)), hydrolyzed cellulose, or a polymer (including polyethylene glycol). In embodiments wherein chitosan is used as a carrier, the chitosan may be dissolved using known methods including in water, in mildly acidic aqueous solutions, in acidic solutions.

The carrier may further comprise a hydrogel such as hyaluronic acid, dextran, pluronic block copolymers of polyethylene oxide and polypropylene, and others. Suitable polyhodroxy compounds include such classes of compounds as acyclic polyhydric alcohols, non-reducing sugars, sugar alcohols, sugar acids, monosaccharides, disaccharides, water-soluble or water dispersible oligosaccharides, polysaccharides and known derivatives of the foregoing. An example carrier comprises glyceryl monolaurate dissolved in glycerol or a 4:1 to 1:4 weight mixture of glycerol and propylene glycol. Reference is made to U.S. Pat. Nos. 5,284,655 and 5,314,476 for other carriers including polyhydroxy carriers, to U.S. Pat. No. 6,884,778 for biocompatible macromers that may be used as carriers, and to U.S. Patent Publication No. 2003/0152548 for cross-linkable monomers that may be used as carriers, all herein incorporated by reference. Settable materials may be used, and they may set up either in situ, or prior to implantation. Optionally, xenogenic bone powder carriers also may be treated with proteases such as trypsin. Xenogenic carriers may be treated with one or more fibril modifying agents to increase the intraparticle intrusion volume (porosity) and surface area. Useful agents include solvents such as dichloromethane, trichloroacetic acid, acetonitrile and acids such as trifluoroacetic acid and hydrogen fluoride. The choice of carrier may depend on the desired characteristics of the composition. In some embodiments, a lubricant, such as water, glycerol, or polyethylene glycol may be added.

Any suitable shape, size, and porosity of carrier may be used. In some embodiments, the carrier may be settable and/or injectable. Such carrier may be, for example, a polymeric cement, a settable calcium phosphate, a settable poly vinyl alcohol, a polyurethane, or a liquid settable polymer. Suitable settable calcium phosphates are disclosed in U.S. Pat. Nos. 5,336,264 and 6,953,594, which are hereby incorporated by reference. Hydrogel carriers may additionally impart improved spatial properties, such as handling and packing properties, to the osteoconductive composition. An injectable carrier may be desirable where the composition is used with a containment device. In addition, selected materials must be biocompatible in vivo and optionally biodegradable. In some uses, the carrier acts as a temporary scaffold until replaced by new bone. Polylactic acid (PLA), polyglycolic acid (PGA), and various combinations have different dissolution rates in vivo. In bone, the dissolution rates can vary according to whether the composition is placed in cortical or trabecular bone.

The carrier may comprise a shape-retaining solid made of loosely adhered particulate material, e.g., with collagen. It may alternatively comprise a molded, porous solid, a monolithic solid, or an aggregate of close-packed particles held in place by surrounding tissue. Masticated muscle or other tissue may also be used. Large allogenic bone implants may act as a carrier, for example where their marrow cavities are cleaned and packed with DBM and, optionally, the osteoinductive factors.

One way to protect small size particles from cellular ingestion and/or to provide a diffusion barrier is to embed them in a monolithic bioabsorbable matrix, and then fragment the particle-containing monolithic matrix into particle sizes greater than 70 microns, for example, greater than 100 microns, or greater than 150 microns in their smallest dimension. Suitable matrices for embedding DBM compositions include biocompatible polymers and setting calcium phosphate cements. Generally the DBM composition/polymer weight ratio will range from about 1:5 to about 1:3. In the case of calcium phosphate, the DBM may be present up to 75% by weight. In one embodiment, DBM is embedded in a resorbable polymer. In a further embodiment, partially demineralized bone particles are embedded in one of the setting calcium phosphates known to the art.

The carrier may comprise a number of materials in combination, some or all of which may be in the form of fibers and/or particles. The carrier may comprise calcium phosphates. Driessens et al. "Calcium phosphate bone cements," Wise, D. L., Ed., Encyclopedic Handbook of Biomaterials and Bioengineering, Part B, Applications New York: Marcel Decker; Elliott, Structure and Chemistry of the Apatites and Other Calcium Phosphates Elsevier, Amsterdam, 1994, each of which is incorporated by reference. Calcium phosphate matrices include, but are not limited to, dicalcium phosphate dihydrate, monetite, tricalcium phospate, tetracalcium phosphate, hydroxyapatite, nanocrystalline hydroxyapatite, poorly crystalline hydroxyapatite, substituted hydroxyapatite, and calcium deficient hydroxyapatites.

In one embodiment, the carrier comprises an osteoinductive material such as a mineralized particulated material, osteoinductive growth factors, or partially demineralized bone. The mineralized particulated material may be TCP, hydroxyapatite, mineral recovered from bone, cancellous chips, cortical chips, surface demineralized bone, or other material. The osteoinductive material may be combined with a further carrier such as starch or glycerol. Accordingly, in some embodiments, the partially demineralized bone may act as a carrier for the tissue-derived extract.

The DBM composition may be completely insoluble or may be slowly solubilized after implantation. Following implantation, the composition may resorb or degrade, remaining substantially intact for at least one to seven days, or for two or four weeks or longer and often longer than 60 days. The composition may thus be resorbed prior to one week, two weeks, three weeks, or other, permitting the entry of bone healing cells.

Formation of an Implant

The DBM provided herein may be used to form an osteoinductive implant. The osteoimplant resulting from the mixture of periosteum tissue and DBM, additive, and/or carrier may be flowable, have a putty consistency, may be shaped or molded, and/or may be deformable. The osteoimplant may assume a determined or regular form or configuration such as a sheet, plate, disk, tunnel, cone, or tube, to name but a few. Prefabricated geometry may include, but is not limited to, a crescent apron for single site use, an I-shape to be placed between teeth for intra-bony defects, a rectangular bib for defects involving both the buccal and lingual alveolar ridges, neutralization plates, reconstructive plates, buttress plates, T-buttress plates, spoon plates, clover leaf plates, condylar plates, compression plates, bridge plates, or wave plates. Partial tubular as well as flat plates can be fabricated from the osteoimplant. Such plates may include such conformations as, e.g., concave contoured, bowl shaped, or defect shaped. The osteoimplant can be machined or shaped by any suitable mechanical shaping means. Computerized modeling can provide for the intricately-shaped three-dimensional architecture of an osteoimplant custom-fitted to the bone repair site with great precision. In embodiments wherein the osteoimplant is shaped or moldable, the implant may retain coherence in fluids.

Accordingly, the osteoinductive DBM composition may be subjected to a configuring step to form an osteoimplant. The configuring step can be employed using conventional equipment known to those skilled in the art to produce a wide variety of geometries, e.g., concave or convex surfaces, stepped surfaces, cylindrical dowels, wedges, blocks, screws, and the like. A surgically implantable material fabricated from elongated bone particles that have been demineralized according to the invention, which may be shaped as a sheet, and processes for fabricating shaped materials from demineralized bone particles is disclosed in U.S. Pat. Nos. 5,507,813 and 6,436,138, respectively, the contents of which are herein incorporated by reference. Suitable sheets include those sold under the trade name Grafton®. DBM Flex, which must be wetted/hydrated prior to use to be useful for implantation. Such sheets have recently been reported as effective in seeding human bone marrow stromal cells (BMSCs), which may be useful in the repair of large bone defects. Kasten et al., "Comparison of Human Bone Marrow Stromal Cells Seeded on Calcium-Deficient Hydroxyapatite, Betatricalcium Phosphate and Demineralized Bone Matrix," Biomaterials, 24(15):2593-603, 2003. Also useful are demineralized bone and other matrix preparations comprising additives or carriers such as binders, fillers, plasticizers, wetting agents, surface active agents, biostatic agents, biocidal agents, and the like. Some exemplary additives and carriers include polyhydroxy compounds, polysaccharides, glycosaminoglycan proteins, nucleic acids, polymers, polaxomers, resins, clays, calcium salts, and/or derivatives thereof.

In some embodiments, the osteoinductive DBM composition prepared from a mixture of periosteum tissue and DBM may be placed in a containment device such as a porous mesh to provide a delivery system. In various embodiments, the device may comprise a polymer (such as polyalkylenes (e.g., polyethylenes, polypropylenes, etc.), polyamides, polyesters, polyurethanes, poly(lactic acid-glycolic acid), poly(lactic acid), poly(glycolic acid), poly(glaxanone), poly(orthoesters), poly(pyrolicacid), poly(phosphazenes), L-co-G, etc.),other bioabsorbable polymer such as Dacron or other known surgical plastics, a natural biologically derived material such as collagen, a ceramic (with bone-growth enhancers, hydroxyapatite, etc.), PEEK (polyether-etherketone), dessicated biodegradable material, metal, composite materials, a biocompatible textile (e.g., cotton, silk, linen), or other. In one embodiment, the containment device is formed as a long bag-like device and may be used with minimally invasive techniques.

In various embodiments, a kit is provided that may include additional parts along with the DBM to be used to implant the DBM mixture with periosteum tissue. The kit may include the DBM mixture with periosteum tissue in a first compartment. The second compartment may include a biodegradable carrier and the growth factor and any other instruments needed for the implanting the DBM. A third compartment may include gloves, drapes, wound dressings and other procedural supplies for maintaining sterility during the implanting process, as well as an instruction booklet. A fourth compartment may include additional tools for implantation (e.g., drills, drill bits, bores, punches, etc.). Each tool may be separately packaged in a plastic pouch that is radiation sterilized. A fifth compartment may comprise an agent for radiographic imaging or the agent may be disposed on the DBM and/or carrier to monitor placement and tissue growth. A cover of the kit may include illustrations of the implanting procedure and a clear plastic cover may be placed over the compartments to maintain sterility.

Uses

The implant prepared from the mixture with periosteum tissue and DBM may be applied at a bone repair site, for example, a site resulting from injury, defect brought about during the course of surgery, infection, malignancy, or developmental malformation. In some embodiments, the implant may be applied at a site wherein the implant has a load-bearing function. The implant may be used for treatment of metabolic bone disease, bone healing, cartilage repair, spinal disc repair, tendon repair, repair of a defect created by disease or surgery, dural repair and may be further used in a wide variety of orthopedic, periodontal, neurosurgical, and oral and maxillofacial surgical procedures. Examples of applications requiring a structural graft include intercalary grafts, spinal fusion, joint plateaus, joint fusions, or large bone reconstructions. Large implants having osteoclast stimulating properties may contribute to the healing process. The implant may further be used in veterinary applications.

The implant prepared from a mixture of DBM with periosteum tissue may further be used as drug delivery device, for example, to deliver factors or agents that promote wound healing. The implant may alternatively or additionally be used to deliver other pharmaceutical agents including antibiotics, anti-neoplastic agents, growth factors, hemopoietic factors, nutrients, or other bioactive agents described above. The amount of the bioactive agent included with the implant can vary widely and will depend on such factors as the agent being delivered, the site of administration, and the patient's physiological condition. The optimum levels are determined in a specific case based upon the intended use of the implant.

At the time just prior to placement of the implant in a defect site, optional materials, e.g., autograft bone marrow aspirate, autograft bone, preparations of selected autograft cells, autograft cells containing genes encoding bone promoting action can be combined with the implant. The implant can be implanted at the bone repair site, if desired, using any suitable affixation means, e.g., sutures, staples, bioadhesives, screws, pins, rivets, other fasteners and the like or it may be retained in place by the closing of the soft tissues around it.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A method for repairing a bone defect, the method comprising applying to the bone defect a substantially effective amount of an osteoinductive composition comprising a mixture of isolated periosteum tissue and demineralized bone matrix, wherein the isolated periosteum tissue has an inner cambium layer, the amount of the isolated periosteum tissue being from about 0.5% by wt. to about 10% by wt. based on a total weight of the osteoinductive composition.

2. A method for repairing a bone defect of claim 1, wherein the isolated periosteum tissue comprises (i) a surface of bone tissue or (ii) long bones comprising femur, tibia, humerus or a mixture thereof.

3. A method for repairing a bone defect of claim 1, wherein the isolated periosteum tissue comprises thin sheets from the surface of bones.

4. A method for repairing a bone defect of claim 1, wherein the osteoinductive composition comprises minced periosteum particles and/or fibers.

5. A method for repairing a bone defect of claim 4, wherein the minced periosteum particles are placed in a chemical bath prior to mixing with the demineralized bone matrix.

6. A method for repairing a bone defect of claim 4, wherein the periosteum tissue is subjected to a terminal sterilization or an aseptic process.

7. A method for repairing a bone defect of claim 4, wherein the periosteum particles and the demineralized bone matrix are mixed and terminally sterilized.

8. A method for repairing a bone defect of claim 1, wherein the periosteum tissue comprises periosteum cells that adhere to the demineralized bone matrix.

9. A method for repairing a bone defect of claim 1, wherein the demineralized bone matrix comprises a plurality of surface demineralized or fully demineralized bone fibers, bone chips, bone particles or mixtures thereof.

10. A method for repairing a bone defect of claim 1, wherein the osteoinductive composition further comprises an osteoinductive and/or osteopromotive additive containing a bone marrow aspirant, blood, a blood product, a bone morphogenetic protein, a growth factor or mixtures thereof.

11. A method for repairing a bone defect of claim 1, wherein the osteoinductive composition further comprises calcium phosphate, collagen, collagen-derivatives, calcium sulfate, silicon containing ceramic, naturally-derived allogenic bone mineral, naturally-derived autogenic bone mineral, fully mineralized bone material or mixtures thereof.

12. A method for repairing a bone defect of claim 1, wherein the osteoinductive composition is added to a delivery vehicle.

13. A method for repairing a bone defect, the method comprising applying to the bone defect a substantially effective amount of an osteoinductive composition comprising a mixture of isolated periosteum tissue and demineralized bone matrix, wherein the isolated periosteum tissue has an inner cambium layer, the amount of the isolated periosteum tissue being from about 0.5% by wt. to about 10% by wt. based on a total weight of the osteoinductive composition, wherein the demineralized bone matrix is prepared separately from the isolated periosteum tissue, wherein the demineralized bone matrix comprises a plurality of surface demineralized or fully demineralized bone fibers, bone chips, bone particles or mixtures thereof.

* * * * *